(12) United States Patent
Brewer

(10) Patent No.: US 6,566,145 B2
(45) Date of Patent: May 20, 2003

(54) DISPOSABLE PIPETTE EXTRACTION

(76) Inventor: William E Brewer, 26 Cedar Field Ct., Columbia, SC (US) 29212

( * ) Notice: Subject to any disclaimer, the term of this patent is extended or adjusted under 35 U.S.C. 154(b) by 70 days.

(21) Appl. No.: 09/780,885

(22) Filed: Feb. 9, 2001

(65) Prior Publication Data

US 2002/0009809 A1 Jan. 24, 2002

Related U.S. Application Data

(60) Provisional application No. 60/181,340, filed on Feb. 9, 2000.

(51) Int. Cl.[7] .................................................. B01L 3/02
(52) U.S. Cl. ...................... 436/178; 422/100; 422/101; 73/864.01; 210/661
(58) Field of Search ................................ 436/178, 180; 422/100, 101; 73/864.01; 210/661

(56) References Cited

U.S. PATENT DOCUMENTS

| | | |
|---|---|---|
| 4,151,089 A | 4/1979 | Ito |
| 5,042,502 A * | 8/1991 | Guirguis |
| 5,171,537 A * | 12/1992 | Wainwright et al. |
| 5,368,729 A | 11/1994 | Stefkovich et al. |
| 5,437,979 A * | 8/1995 | Rampal et al. |
| 5,443,734 A | 8/1995 | Fetner et al. |
| 5,512,168 A | 4/1996 | Fetner et al. |
| 5,529,694 A | 6/1996 | Strickler |
| 5,595,653 A | 1/1997 | Good et al. |
| 5,660,792 A | 8/1997 | Koike |
| 5,849,249 A | 12/1998 | Jones, Jr. et al. |
| 5,874,004 A | 2/1999 | DeWitt |
| 5,888,409 A | 3/1999 | Morsiani et al. |
| 6,048,457 A | 4/2000 | Kopaciewicz et al. |
| 6,117,394 A * | 9/2000 | Smith |

OTHER PUBLICATIONS

ZipTip Pippette Tips at <<http://www.millipore.com/catalogue.nsf/docs/C5737>> is an online catalog of biological filtration devices. Here, pipette tips having a polymer–bound extractions medium are disclosed.

* cited by examiner

*Primary Examiner*—Jan Ludlow
(74) *Attorney, Agent, or Firm*—Michael A. Mann; Sara A. Centioni; Nexsen Pruet Jacobs & Pollard, LLC

(57) ABSTRACT

The present invention is a disposable apparatus for the rapid, low-volume solid phase extraction of analytes from a variety of sources. The apparatus of the present invention is configured as a pipette tip and contains a loosely confined stationary phase. The mobility of the stationary phase particles enables rapid mixing and equilibration with a sample solution during agitation. The analyte may thereby be extracted in less time with less solvent, removing the need for a separate concentration step.

19 Claims, 4 Drawing Sheets

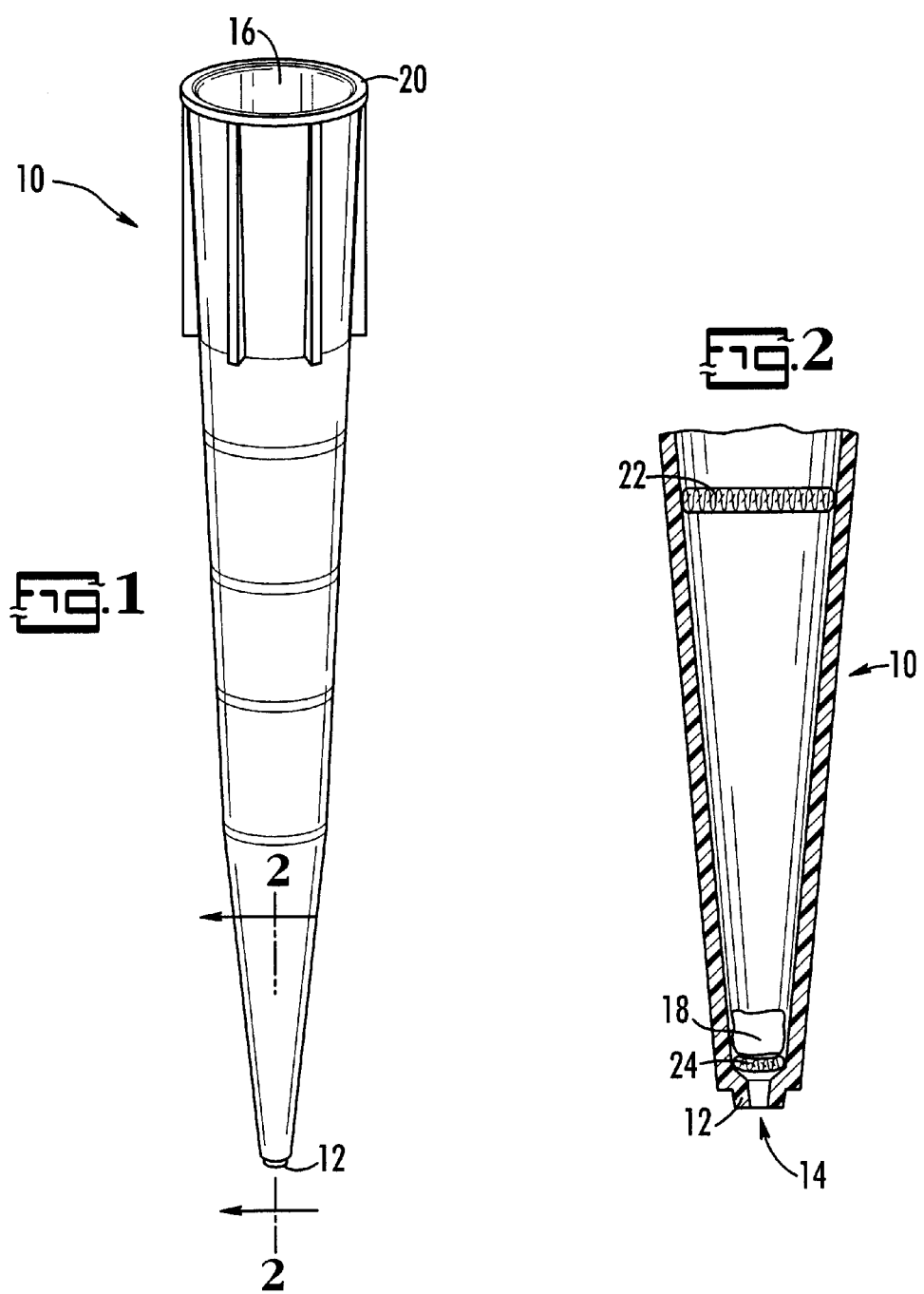

DISPOSABLE PIPETTE EXTRACTION

PRIORITY CLAIM

The applicant claims the benefit of the filing date of provisional application No. 60/181,340 filed Feb. 9, 2000.

FIELD OF THE INVENTION

The present invention relates to an apparatus for rapid, disposable, low volume solid phase extraction and to a method for using such an apparatus.

DISCUSSION OF BACKGROUND

Solid Phase Extraction (SPE) has become popular in sample preparation. The main advantage of SPE is that less solvent is required as compared to traditional liquid extraction. In SPE, a cartridge composed of plastic is used to store the adsorptive particle of stationary phase as well as to provide a sample reservoir. The cartridge is placed on a vacuum manifold, and the vacuum is used to pull sample and solvent through the stationary phase. The stationary phase is first washed and activated by addition of various solvents (approximately 1–3 mL each) in a conditioning step. The conditioning step is also essential to prevent channeling, a process in which the sample components pass though the stationary phase packing without actually interacting with the adsorptive particles of the stationary phase in a chemically-meaningful manner.

The sample matrix is subsequently added to the cartridge, and the matrix is passed slowly though the stationary phase to allow the analyte to interact with the stationary phase. Several types of analyte-stationary phase interactions are possible, such as adsorption and partitioning. After the sample matrix has passed through the cartridge to waste, a wash step is performed to remove compounds of the sample matrix. The final step is elution of the analytes. A clean test tube is first placed under the SPE cartridge, then elution solvent (1–2 mL) is added to remove the analytes from the stationary phase.

After the extraction procedure, a concentration step is performed to improve the sensitivity of analysis. The solvent from the extract (1–2 mL) is evaporated using nitrogen gas flow and heat. A small volume of solvent (0.10–0.20 mL) is then added to the test tube, and the test tube is vortexed to dissolve the extracted analytes. The solution is subsequently transferred to a clean vial for analysis by gas chromatography (GC) or high performance liquid chromatography (HPLC).

Although SPE has helped to make sample preparation faster and easier, the concentration step by itself takes several minutes to perform, with the entire extraction time taking over 20 minutes. Another drawback to SPE is that significant solvent volumes are still required (at least 5 mL total). An extraction procedure that significantly reduces the extraction time and reduces solvent volume will have a significant impact in analytical preparation methods.

There have been numerous attempts to remedy the foregoing deficiencies in SPE. A notable modification of this technology is disclosed in U.S. Pat. No. 6,048,457 issued to Kopaciewicz et al. This patent discloses a method of SPE that uses a polymer-matrix bound sorbent material. In one embodiment, a porous polymer matrix entraps particles of adsorbent material and is cast-in-place inside a pipette tip. In a contrasting example, sorbent particles are immobilized between two porous frits. This invention provides an effective platform for micromass handling. Unfortunately, the matrix-bound particles are unable to achieve maximum contact with the sample solution due to minimal exposed surface area and severely restricted mobility of the particles. As a result, the efficiency of the solid-liquid equilibrium leaves much room for improvement.

Therefore, there still exists a substantial need for a chemical extraction device that adequately overcomes the problems existing in preparing chemical samples for chromatographic separation techniques.

SUMMARY OF THE INVENTION

According to its major aspects and broadly stated, the present invention is a device for rapid, disposable, low-volume solid phase extraction of analytes from various fluids to be tested. The term fluid refers to liquids and to semi-liquids. In particular, the present invention relates to a pipette tip which contains adsorptive particles of a solid stationary phase that are loosely confined inside the tip. An attached pipettetor draws the sample into the pipette tip. The present invention is also a method for using the foregoing pipette tip to extract an analyte. Maximum contact and thorough mixing between the stationary phase and the analyte solution is accomplished by agitating them (shaking, inverting repeatedly, vortexing or by drawing air into the pipette). Agitation insures rapid equilibration and, thus, efficient and rapid adsorption of the analyte.

Other features and advantages of the present invention will be apparent to those skilled in the art from a careful reading of the Detailed Description of a Preferred Embodiment accompanied by the following drawings.

BRIEF DESCRIPTION OF THE DRAWINGS

In the drawings,

FIG. 1 is a front view of a typical pipette tip which can be used with a pipettor.

FIG. 2 is a detailed cross-sectional view along line 2 of FIG. 1 of a preferred embodiment of the present invention;

DETAILED DESCRIPTION OF A PREFERRED EMBODIMENT

Figure 3:
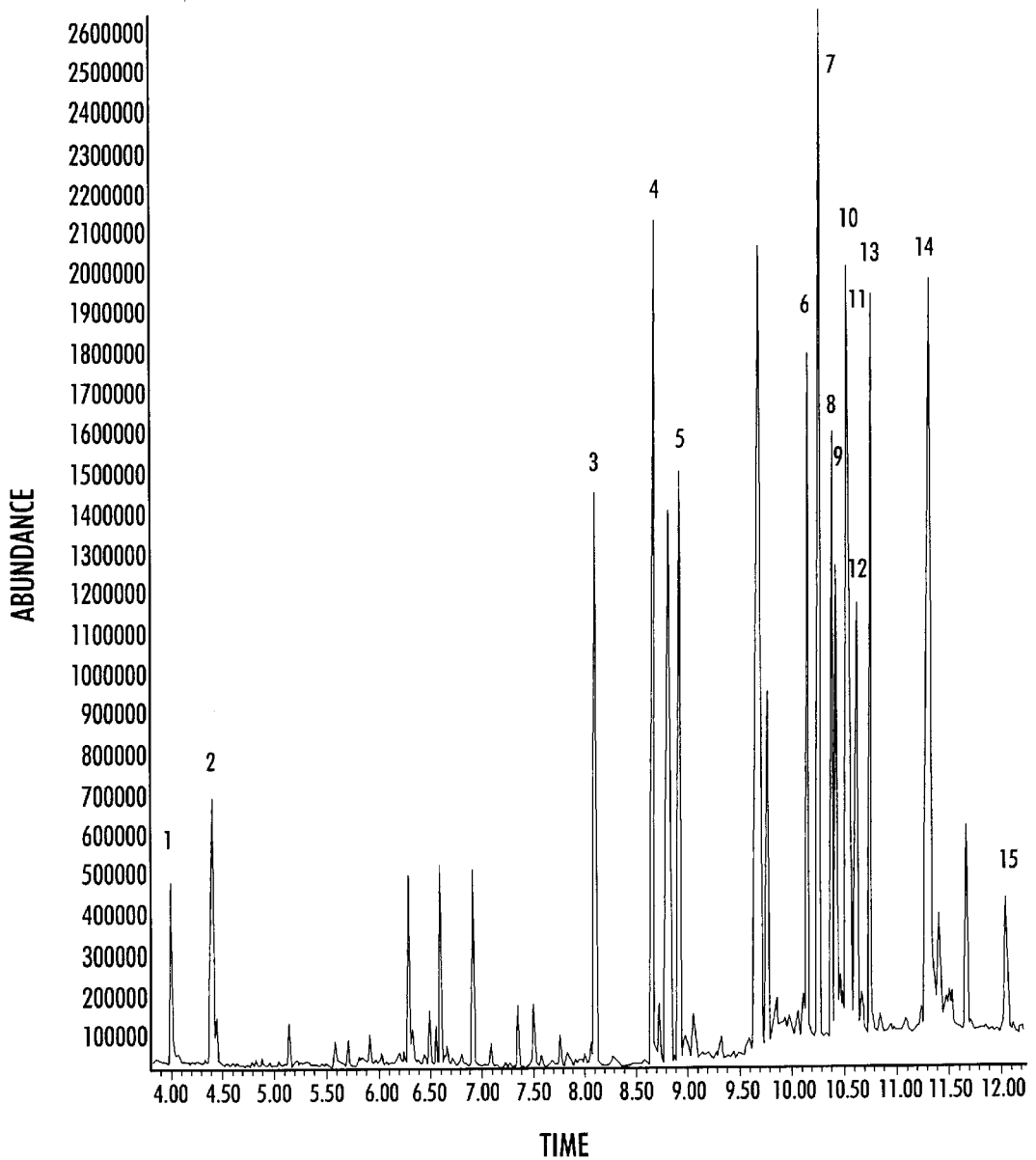
FIG. 3 is a chromatogram of a drug mixture extracted from serum using the disposable pipette tip of the present invention.

The present invention is a disposable pipette tip extraction apparatus for use in rapid, disposable, and low-volume solid phase extraction of analytes.

With reference to FIG. 1 and FIG. 2, a typical pipette tip 10 is shown having a proximal end 12 with lower opening 14 and a distal end 20 with upper opening 16. Pipette tip 10 can be made of any inexpensive material or commodity plastic, but is preferably made from a polyolefin, and most preferably made from polyethylene, polypropylene, polyethylene-terephthalate, or polytetrafluoroethylene. The distal end 20 is configured to fit on the end of a standard laboratory pipettor. The proximal end 12 is configured to allow the passage of whatever fluid one wishes to sample with the pipettor. Moreover, the pipette tip is preferably conical in shape, with distal end 20 having a larger internal diameter than proximal end 12.

FIG. 2 shows a cross section of an embodiment of the present invention. Within the lumen of pipette tip 10 is first frit 24. The purpose of first frit 24 is to provide a permeable barrier which permits the unrestricted passage of fluids in either direction but does not allow the stationary phase material to pass through, thereby insuring that no loss of stationary material occurs. First frit 24 can be a sintered glass plug, a glass wool plug, a porous polymer plug, or a metal screen. A second frit 22 is located between first frit 24 and distal end 20. Second frit 22 is optional. The purpose of second frit 22 is to prevent the passage of either solids or fluids therethrough; this insures the retention of the stationary phase within and contamination of the pipette tip and the fluid below second frit 22, and prevents contamination of the pipettor by sample solution or solvents during the agitation step. Second frit 22 is preferably a sintered glass plug, a porous polymer plug, or a semi-permeable membrane First frit 24 and second frit 22 are spaced apart so as to form a void therebetween; this void can function as a mixing chamber for the various components of the present invention. Confined in the void formed between first frit 24 and second frit 22 are adsorptive particles of stationary phase 18. Stationary phase 18 is selected to have an affinity for the desired analyte and may be any suitable material which may be used in standard solid phase extraction techniques. Preferably, stationary phase 18 is silica, derivitized silica, polystyrene-divinylbenzene copolymer, functionalized polystyrene-divinylbenzene copolymer, or activated carbon. The particles of stationary phase 18 may freely travel between first frit 24 and second frit 22 such as, for example, during agitation; free movement between first and second frits 24, 22, respectively, allows for maximum contact and thorough mixing with the sample fluid and rapid equilibration through agitation.

The present invention is also a method for using the foregoing pipette tip to extract an analyte from a sample solution.

Pipette tip 10 is attached to a standard laboratory pipettor, and a volume of sample liquid is drawn into pipette tip 10 so the sample liquid is in physical contact with the adsorptive particles of stationary phase 18. In order to achieve maximum contact and thorough mixing between stationary phase 18 and the sample fluid, the pipette tip and attached pipettor are agitated. This can be accomplished by shaking or inverting repeatedly, but is accomplished preferably by vortexing with a common laboratory vortexer. Such agitation insures rapid equilibration and, thus, efficient and rapid adsorption of the analyte by stationary phase 18.

The sample liquid is then expelled to waste from pipette tip 10 through lower opening 14 in proximal end 12. Next, an optional wash step can be rapidly performed by drawing up wash solvent (e.g. water), agitating the resulting solvent/stationary phase mixture, and expelling the wash solution to waste. The analyte is then removed from stationary phase 18 by drawing a small volume of extraction solvent into pipette tip 10 and agitating as before. The resulting analyte solution is then expelled from pipette tip 10. It is notable that the solution may be immediately analyzed by conventional laboratory techniques, without the need for a concentration step; the efficiency of the equilibration insures that the analyte solution is of high concentration and may be analyzed directly. Pipette tip 10 may be removed from the pipettor and disposed of.

The present method is further described by the following examples.

EXAMPLE 1—DPX

A pipette tip (1 mL) was fitted with a frit at the bottom. Stationary phase (10 mg, Oasis® HLB, Waters Corp.) was added to the pipette tip (FIG. 2). The stationary phase was activated by adding methanol and water. Only 0.20 mL methanol was drawn into the pipette tip using a pipettor. The methanol was vortexed with stationary phase for 5 sec., then the methanol was delivered to a waste container. The activation was completed by drawing 0.20 mL water, vortexing for 5 sec., and delivering the water to waste. The serum sample (0.5 mg/L SPE drug mix) was extracted by drawing 0.50 mL serum into the tip. The sample was then vortexed for 20 sec. The serum was subsequently delivered to waste. The wash step was performed by drawing 0.50 mL water into the tip, vortexing for 10 sec., and delivering the water to waste. Elution of adsorbed analytes was performed by drawing 0.15 mL of 20% methanol in ethyl acetate, vortexing for 10 sec., and delivering the solution to a vial. This procedure was repeated with an additional 0.15 mL of elution solvent. A disposable glass pipette was then used to draw the extract solution, a few drops were sent to waste to remove unwanted water content, and the solution was transferred to a vial insert.

The extract was injected into a GC/MS instrument directly (FIG. 3), without any concentration step. The total extraction time took approximately 3 minutes to perform. This extraction is referred to as disposable pipette extraction (DPX). DPX provides a means for thoroughly and rapidly mixing the stationary phase with sample and solvent. The used pipette tip is subsequently disposed of, and a new one is added to the pipettor to begin subsequent extractions. The results are shown in FIG. 3 as follows: 1. Amphetamine; 2. Methamphetamine; 3. Meperidine; 4. Glutehimide; 5. Phencyclidine (PCP); 6. Methadone; 7. Methaqualone; 8. Amitriptyline; 9. Cocaine; 10. Imipramine; 11. Doxepin; 12. Desipramine; 13. Pentazocine; 14. Codeine; and 15. Oxycodone.

EXAMPLE 2—DPX

Figure 4:
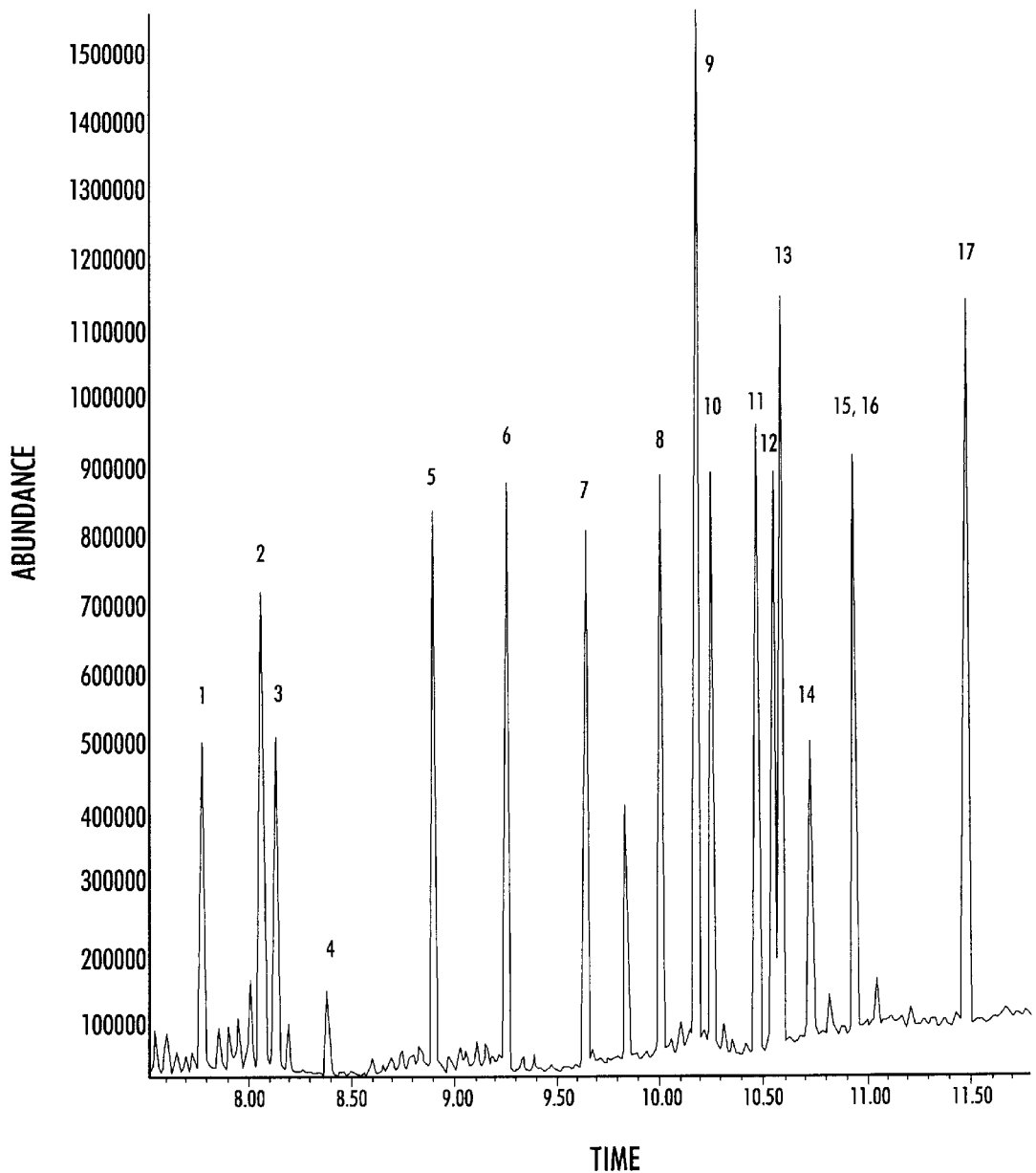
FIG. 4 is a chromatogram of an organochlorine pesticide mixture extracted from a mixture of acetonitrile and water using the disposable pipette tip of the present invention.

The same protocol was followed as described in Example 1, above, but the extraction was from 2 mL of a mixture of acetonitrile and water (65/35) and the organochlorine pesticide concentration was 1.0 ppm. The sample was first evaporated to less than 1 mL with nitrogen gas flow, then the sample was extracted by DPX in less than 5 minutes using 0.20 mL of organic solvent. A concentration step was not performed. The results are shown in FIG. 4 as follows: 1. $\alpha$-BHC; 2. $\alpha$-BHC; 3. $\alpha$-BHC; 4. $\alpha$-BHC; 5. Heptachlor; 6. Aldrin; 7. Heptachlor epoxide; 8. Endosulfan; 9. p,p'-DDE; 10. Dieldrin; 11. Endrin; 12. Endosulfan; 13. p,p'-DDD; 14. Endrin aldehyde; 15. p,p'-DDT; 16. Endosulfan sulfate; and 17. Methoxychlor.

EXAMPLE 3—DPX

Figure 5:
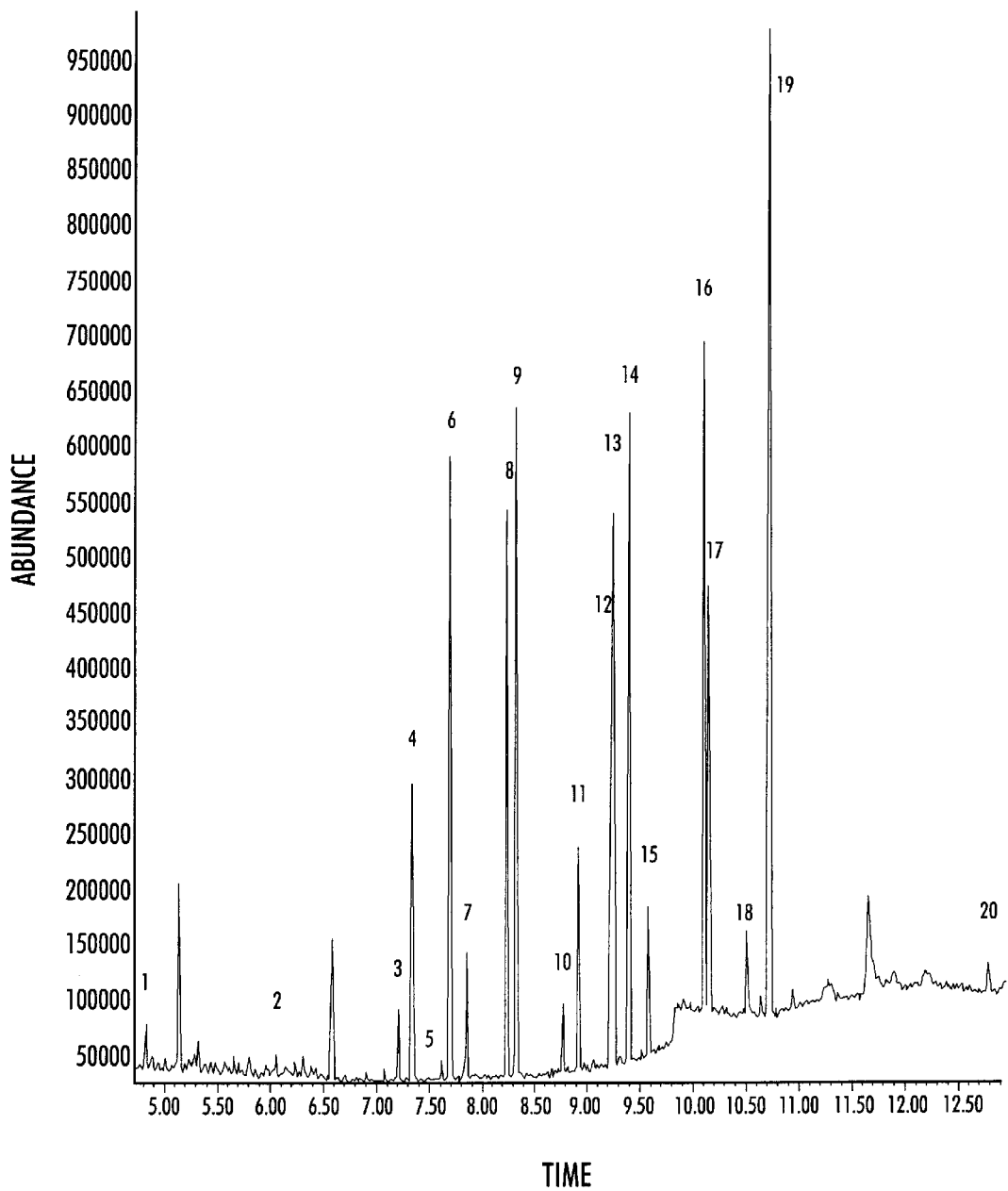
FIG. 5 is a chromatogram of an organophosphorous pesticide mixture extracted from a mixture of acetonitrile and water using the disposable pipette tip of the present invention.

The same protocol as described in Example 1, above, except that the analyte was an organophosphorous pesticide mixture (1.0 ppm). The results are shown in FIG. 5 as follows: 1. Dichlorvos; 2. Mevinphos; 3. Ethoprophos; 4. Naled; 5. Phorate; 6. Demeton; 7. Diazinon; 8. Disulfoton; 9. Methyl azinphos; 10. Methyl parathion; 11. Ronnel; 12. Fenthion; 13. Chlorpyrifos; 14. Trichloronate; 15. Stirofos; 16. Prothiofos; 17. Merphos; 18. Fensulfothion; 19. Bolstar; and 20. Coumaphos.

It will be clear to those skilled in the art of analytical chemistry that many modifications and substitutions can be made without departing from the spirit and scope of the invention, which is defined by the appended claims.

What is claimed is:

1. A pipette tip for solid phase extraction comprising:
   a housing having a proximal end with a lower opening adapted for the passage of liquid and a distal end with an upper opening dimensioned to fit on the end of a pipettor;
   a first frit inside said housing and above said lower opening;
   a second frit inside said housing and between said first frit and said upper opening; and
   a plurality of adsorptive particles inside said housing and confined between said first frit and said second frit, wherein said adsorptive particles and said second frit are spaced apart so as to form a void therebetween, and wherein said void is dimensioned so that said adsorptive particles can travel freely within said void allowing for thorough mixing between said adsorptive particles and a sample solution when said sample solution is in said void.

2. The pipette tip as recited in claim 1, wherein said void is dimensioned so that a quantity of air can be drawn in through said pipette tip for agitation of said adsorptive particles and said sample solution.

3. The pipette tip as recited in claim 1, further comprising means for agitating that is operatively connected to said housing.

4. The pipette tip as recited in claim 1, wherein said first frit is permeable by gases and liquids, but not solids.

5. The pipette tip as recited in claim 1, wherein said first frit is selected from the group consisting of sintered glass plug, glass wool plug, porous polymer plug, and metal screen.

6. The pipette tip as recited in claim 4, wherein said second frit is permeable by gases, but not liquids or solids.

7. The pipette tip as recited in claim 4, wherein said second frit is selected from the group consisting of sintered glass plug, porous polymer plug, and semi-permeable membrane.

8. The pipette tip as recited in claim 1, wherein said housing comprises a material selected from the group consisting of polyethylene, polypropylene, polyethylene-terephthalate, and polytetrafluoroethylene.

9. The pipette tip as recited in claim 1, wherein said adsorptive particles comprise a material selected from the group consisting of silica, derivitized silica, polystyrene-divinylbenzene copolymer, functionalized polystyrene-divinylbenzene copolymer, and activated carbon.

10. The pipette tip as recited in claim 1, wherein said housing comprises a material selected from the group consisting of polyethylene, polypropylene, polyethylene-terephthalate, and polytetrafluoroethylene.

11. The pipette tip as recited in claim 1, wherein said adsorptive particles comprise a material selected from the group consisting of silica, derivitized silica, polystyrene-divinylbenzene copolymer, functionalized polystyrene-divinylbenzene copolymer, and activated carbon.

12. A process for extracting an analyte from a liquid, said process comprising the steps of:
    providing a pipette tip with a housing having a lower opening adapted for the passage of liquid and a distal end with an upper opening dimensioned to fit on the end of a pipettor, a first frit inside said housing and above said lower opening, and a plurality of adsorptive particles inside said housing and confined between said first frit and said upper opening, wherein said adsorptive particles and said upper opening are spaced apart so as to form a void therebetween, and wherein said void is dimensioned so that said adsorptive particles can travel freely within said void allowing for thorough mixing between said adsorptive particles and a sample solution when said sample solution is in said void;
    attaching said pipette to a pipettor;
    drawing a sample liquid into said pipette tip so that said liquid is in physical contact with said adsorptive particles;
    agitating said liquid sample in said pipette tip, wherein said agitating step is selected from the group consisting of shaking said liquid sample, vortexing said liquid sample, and drawing air into said liquid sample;
    expelling said sample liquid from said pipette tip;
    adding extraction solvent into said pipette tip so said extraction solvent is in physical contact with said adsorptive particles; and
    expelling said extraction solvent from said pipette tip.

13. The process for extracting an analyte from a liquid as recited in claim 12, wherein said process is conducted without a concentration step.

14. The process for extracting an analyte from a liquid as recited in claim 12, said process further comprising the step of disposing of said pipette tip.

15. The process for extracting an analyte from a liquid as recited in claim 12, said process further comprising the step of analyzing said extraction solvent.

16. The process for extracting an analyte from a liquid as recited in claim 12, wherein said first frit is permeable by gases and liquids, but not solids.

17. The process for extracting an analyte from a liquid as recited in claim 12, wherein said first frit is selected from the group consisting of sintered glass plug, glass wool plug, porous polymer plug, and metal screen.

18. The process for extracting an analyte from a liquid as recited in claim 12, wherein said housing comprises a material selected from the group consisting of polyethylene, polypropylene, polyethylene-terephthalate, and polytetrafluoroethylene.

19. The process for extracting an analyte from a liquid as recited in claim 12, wherein said adsorptive particles comprise a material selected from the group consisting of silica, derivitized silica, polystyrene-divinylbenzene copolymer, functionalized polystyrene-divinylbenzene copolymer, and activated carbon.

* * * * *